(12) United States Patent
Nagata et al.

(10) Patent No.: US 8,110,714 B2
(45) Date of Patent: Feb. 7, 2012

(54) POLYACENE COMPOUND AND ORGANIC SEMICONDUCTOR THIN FILM

(75) Inventors: Kazuto Nagata, Fuji (JP); Yoshinori Naruta, Fukuoka (JP); Masatoshi Yakiyama, Fukuoka (JP)

(73) Assignee: Asahi Kasei Corporation, Osaka-shi, Osaka (JP)

( * ) Notice: Subject to any disclaimer, the term of this patent is extended or adjusted under 35 U.S.C. 154(b) by 1012 days.

(21) Appl. No.: 10/590,727

(22) PCT Filed: Feb. 25, 2005

(86) PCT No.: PCT/JP2005/003111
§ 371 (c)(1),
(2), (4) Date: Aug. 25, 2006

(87) PCT Pub. No.: WO2005/080304
PCT Pub. Date: Sep. 1, 2005

(65) Prior Publication Data
US 2008/0061287 A1 Mar. 13, 2008

(30) Foreign Application Priority Data

Feb. 25, 2004 (JP) ................................. 2004-049879

(51) Int. Cl.
*C07C 22/00* (2006.01)
(52) U.S. Cl. .......... 570/183; 257/40; 556/432; 556/489; 568/306
(58) Field of Classification Search .................. None
See application file for complete search history.

(56) References Cited

U.S. PATENT DOCUMENTS 7,061,010 B2 * 6/2006 Minakata ........................ 257/40

FOREIGN PATENT DOCUMENTS

| EP | 1 416 069 A1 | 5/2004 |
| JP | 2004158719 A * | 6/2004 |
| WO | WO-00/56933 A1 | 9/2000 |
| WO | WO 0056933 A1 * | 9/2000 |
| WO | WO-03/016599 A1 | 2/2003 |
| WO | WO 03016599 A1 * | 2/2003 |

OTHER PUBLICATIONS

Sparfel et al, Tetrahedron, 1980, 36(15), pp. 2225-2235.*
English language abstract of CN 1585151 A (Feb. 23, 2005).
Kato, T. et al., Journal of Chemical Physics, 2003, vol. 119, No. 21, pp. 11318 to 11328.
Christos D. Dimitrakopoulos et al., Adv. Mater. vol. 14, No. 2, pp. 99-117 (2002).
C.D. Dimitrakopoulos et al., J. Appl. Phys., vol. 80 No. 4, Aug. 15, 1996, pp. 2501-2508.
Hagen Klauk et al., I EEE Transaction on Electron Devices, vol. 46, No. 6, Jun. 1999 pp. 1258-1263.
A.R. Brown et al., J. Appl. Phys. vol. 79, No. 4, Feb. 15, 1996, pp. 2136-2138.
Tamotsu Takahashi et al., J. Am. Chem. Soc.122, pp. 12876-12877 (2000).
Ron J. Graham et al., J. Org. Chem. vol. 60, pp. 5770-5777 (1995).
Daniel M. Bowles et al., Organic Letter, vol. 2, No. 1, pp. 85-87 (2000).
Glen P. Miller et al., Organic Letters, vol. 2, No. 25, pp. 3979-3982 (2000).
Hong Meng et al., Adv. Mater., 15, No. 13, pp. 1090-1093 (2003).
Dmitrii F. Perepichka et al., J. Am. Chem. Soc. vol. 125, pp. 10190-10191 (2003).
Kumano Ebihara, "Organic synthesis I- Carbon synthesis. Halogen synthesis-, $4^{th}$ Ed., Lecture 19 in Chemical Experiment", Maruzen Co., Ltd., Jun. 5, 1992 (partial English translation p. 438, line 13 to p. 446, line 6).

* cited by examiner

*Primary Examiner* — Sudhakar Katakam
(74) *Attorney, Agent, or Firm* — Birch, Stewart, Kolasch & Birch, LLP

(57) ABSTRACT

The present invention provides an organic semiconductor material which exhibits a high mobility, and excellent solubility in solvents and oxidation resistance. The present invention also provides an organic semiconductor thin film exhibiting a high mobility, and an organic semiconductor device exhibiting excellent electronic characteristics. A transistor structure is formed by coating the silicon substrate with a thin film of pentacene compound substituted halogens at 6 and 13 positions and aliphatic hydrocarbons at 2, 3, 9 and 10 positions, wherein the substrate is patterned beforehand with gold to have a source and drain electrodes.

15 Claims, 2 Drawing Sheets

POLYACENE COMPOUND AND ORGANIC SEMICONDUCTOR THIN FILM

TECHNICAL FIELD

The present invention relates to an organic semiconductor material, and an organic semiconductor thin film and organic semiconductor device using the organic semiconductor material.

BACKGROUND ART

An organic semiconductor device can be produced under milder film-making conditions than those of a conventional inorganic semiconductor device, and formed into a thin film, or into a film at normal temperature, on various substrates. Therefore, it can be produced at a lower cost, and formed into a thin film on a polymer film or the like, allowing it to remain flexible.

Organic semiconductor materials under development include conjugated polymer compounds and oligomers thereof, e.g., polyphenylene vinylene, polypyrrole and polythiophene; and aromatic compounds centered by polyacene compounds, e.g., anthracene, tetracene and pentacene. In particular, it is reported that polyacene compounds can exhibit a high carrier mobility and excellent semiconductor device characteristics by virtue of high carrier mobility, because of their high crystallinity resulting from high intermolecular cohesion.

Polyacene compounds are applied to devices in the form of deposited film or single crystal. Their applicable areas under development include transistors, photovoltaic cells and lasers, among others (see Non-Patent Documents 1 to 3).

One of the methods other than deposition for forming a thin polyacene film spreads a solution of a precursor for pentacene as one polyacene compound on a substrate and heats it to form a thin pentacene film (see Non-Patent Document 4). A polyacene compound is not highly soluble in a solvent, and the above method uses a more soluble precursor to form a thin film by spreading the precursor solution and then converts the precursor into the polyacene compound under heating.

On the other hand, polyacene compounds with a substituent are discussed by Takahashi et al. (Non-Patent Document 5), Graham et al. (Non-Patent Document 6), Anthony et al. (Non-Patent Document 7) and Miller et al. (Non-Patent Document 8). Moreover, Non-Patent Documents 9 and 10 disclose synthesis of 2,3,9,10-tetramethylpentacene and 2,3,9,10-tetrachloropentacene, respectively.

An organic semiconductor material exceeding pentacene in mobility is not known so far.

However, the method for forming a thin polyacene film by use of the precursor of polyacene compound, e.g., that described above, needs treatment at high temperature to convert the precursor into the polyacene compound (for example about 150° C. in the case of pentacene). Moreover, it is difficult to completely convert a precursor into a corresponding polyacene, with the result that the unreacted precursor may remain as a defect or modified into a defect at high temperature.

On the other hand, Takahashi et al. proposes various polyacene derivatives with one or more substituents. They are however silent on their characteristics as organic semiconductor materials and making their thin films. Moreover, 2,3,9,10-tetramethylpentacene and 2,3,9,10-tetrachloropentacene are synthesized. However, their thin films exhibit a lower mobility than that of pentacene. In particular, the latter is modified in a film-making process carried out at high temperature to fail to exhibit semiconductor properties.

Still more, polyacene compounds tend to lose oxygen or water stability as their number of condensed rings increases. Pentacene, for example, is relatively stable when it is solid, but may be readily oxidized with oxygen into polyacenequinone when it is in the form of solution. This trend is more noted when it has an electron donating group, e.g., alkyl group, at the end of the major axis. Polyacenequinone exhibits no properties as a semiconductor, and a polyacene compound preferably has high oxidation resistance to prevent degradation of properties.

It is an object of the present invention to solve the above problems involved in the conventional techniques and provide an organic semiconductor material exhibiting a high mobility, solubility in solvents and oxidation resistance. The other objects are to provide an organic semiconductor thin film exhibiting a high mobility, and an organic semiconductor device excellent in electronic characteristics.

Non-Patent Document 1: "Advanced Materials," 2002, vol. 14, p. 99
Non-Patent Document 2: Dimitrakopoulos et al., "Journal of Applied Physics," 1996, vol. 80, p. 2501
Non-Patent Document 3: Cloak et al., "IEEE Transaction on Electron Devices," 1999, vol. 46, p. 1258
Non-Patent Document 4: Brown et al., "Journal of Applied Physics," 1996, vol. 79, p. 2136
Non-Patent Document 5: Takahashi et al., "Journal of American Chemical Society," 2000, vol. 122, p. 12876
Non-Patent Document 6: Graham et al., "Journal of Organic Chemistry," 1995, vol. 60, p. 5770
Non-Patent Document 7: Anthony et al., "Organic Letters," 2000, vol. 2, p. 85
Non-Patent Document 8: Miller et al., "Organic Letters," 2000, vol. 2, p. 3979
Non-Patent Document 9: "Advanced Materials," 2003, vol. 15, p. 1090
Non-Patent Document 10: "Journal of American Chemical Society," 2003, vol. 125, p. 10190

DISCLOSURE OF THE INVENTION

The present invention has the following aspects to solve the above problems. More specifically, the polyacene compound of the present invention has a structure represented by the chemical formula (I):

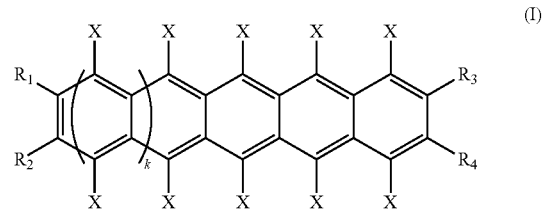

wherein at least one of $R_1$, $R_2$, $R_3$ and $R_4$ in the chemical formula (I) is/are an aliphatic hydrocarbon group (such as an alkyl group, alkenyl group or alkynyl group), aryl group, alkoxy group, aryloxy group, acyl group, ester group, alkyloxycarbonyl group, aryloxycarbonyl group, carboxyl group, formyl group, hydroxyl group, halogen group, amino group, imino group, amide group, cyano group, silyl group, mercapto group, sulfide group, disulfide group or sulfonyl group, or a functional group containing 2 or more groups thereof, and the other(s) is/are a hydrogen atom, some of Xs, that are two or more, are a halogen group and the other(s) is/are a hydrogen atom, and k is an integer of 1 to 5.

$R_3$ and $R_4$ are preferably each hydrogen atom.

It is preferable that at least one of the combinations ($R_1$ and $R_2$) and ($R_3$ and $R_4$) forms a cyclic structure, after $R_1$ and $R_2$ or $R_3$ and $R_4$ are bound to each other.

Moreover, $R_1$, $R_2$, $R_3$ and $R_4$ preferably have 1 to 15, more preferably 2 to 15, and particularly preferably 2 to 6 carbon atoms, when they are functional groups.

It is also preferable that an even number of Xs are each a halogen group, at least 2 of which are bound to the same acene ring. It is particularly preferable that two of Xs are each a halogen group bound to the same acene ring.

Still more, k is preferably 1 or 2.

The organic semiconductor thin film of the present invention is made of a polyacene compound having a structure represented by the following chemical formula (I) and has crystallinity.

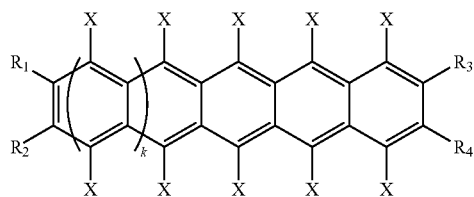
(I)

In the chemical formula (I), at least one of $R_1$, $R_2$, $R_3$ and $R_4$ is/are an aliphatic hydrocarbon group (such as an alkyl group, alkenyl group or alkynyl group), aryl group, alkoxy group, aryloxy group, acyl group, ester group, alkyloxycarbonyl group, aryloxycarbonyl group, carboxyl group, formyl group, hydroxyl group, halogen group, amino group, imino group, amide group, cyano group, silyl group, mercapto group, sulfide group, disulfide group or sulfonyl group, or a functional group containing 2 or more groups thereof, and the other(s) is/are a hydrogen atom. In the chemical formula, some of Xs is/are a halogen group and the other(s) is/are a hydrogen atom. Moreover, k is an integer of 1 to 5.

It is preferable that $R_3$ and $R_4$ in the chemical formula (I) are each a hydrogen atom. It is also preferable that at least one of the combinations ($R_1$ and $R_2$) and ($R_3$ and $R_4$) forms a cyclic structure, after $R_1$ and $R_2$ or $R_3$ and $R_4$ are bound to each other. Moreover, $R_1$, $R_2$, $R_3$ and $R_4$ preferably have 1 to 15, more preferably 2 to 15, particularly preferably 2 to 6 carbon atoms, when they are functional groups. It is also preferable that an even number of Xs are each a halogen group, at least two of which are bound to the same acene ring. It is particularly preferable that two of Xs are each a halogen group bound to the same acene ring. Still more, k is preferably 1 or 2.

It is a crystalline, organic semiconductor thin film formed on a substrate, the major axis of the molecule of the compound preferably being oriented toward a right angle to the substrate surface.

Moreover, at least part of the organic semiconductor device of the present invention is composed of the organic semiconductor thin film of the present invention.

Still more, the transistor of the present invention has a gate electrode, dielectric layer, source electrode, drain electrode and semiconductor layer, wherein the semiconductor layer is composed of the organic semiconductor thin film of the present invention.

The method for producing the polyacene compound of the present invention comprises reducing a polyacenequinone derivative into a hydroxypolyacene derivative, and then halogenating and aromatizing the hydroxypolyacene derivative into a polyacene compound having a structure represented by the above-described chemical formula (I). The polyacenequinone derivative has a chemical structure corresponding to that of a polyacene compound of the above-described chemical formula (I), has the same number of 6-membered rings and the same $R_1$, $R_2$, $R_3$ and $R_4$, and has the carbonyl carbon of quinine, the carbon atom of which will be bound to a halogen group, when it is converted into the polyacene compound. The hydroxypolyacene derivative has a chemical structure corresponding to that of a polyacene compound of the above-described chemical formula (I), has the same number of 6-membered rings and the same $R_1$, $R_2$, $R_3$ and $R_4$, and has a carbon atom bound to a hydroxyl group and hydrogen atom, which will be bound to a halogen group, when it is converted into the polyacene compound.

The method for producing the polyacene compound of the present invention comprises reducing a polyacenequinone derivative having a structure represented by the chemical formula (II) into a hydroxypolyacene derivative having a structure represented by the chemical formula (III), and then halogenating and aromatizing the hydroxypolyacene derivative to produce a polyacene compound having a structure represented by the above-described chemical formula (I),

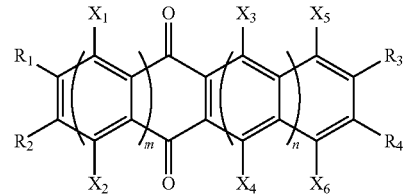
(II)

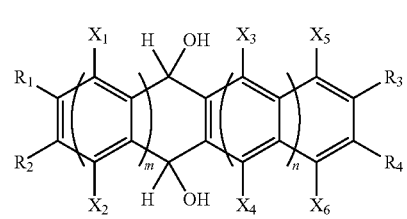
(III)

wherein at least one of $R_1$, $R_2$, $R_3$ and $R_4$ in the chemical formulas (II) and (III) is/are an aliphatic hydrocarbon group (such as an alkyl group, alkenyl group or alkynyl group), aryl group, alkoxy group, aryloxy group, acyl group, ester group, alkyloxycarbonyl group, aryloxycarbonyl group, carboxyl group, formyl group, hydroxyl group, halogen group, amino group, imino group, amide group, cyano group, silyl group, mercapto group, sulfide group, disulfide group or sulfonyl group, or a functional group containing 2 or more groups thereof, and the other(s) is/are a hydrogen atom, $X_1$, $X_2$, $X_3$, $X_4$, $X_5$ and $X_6$ in the chemical formulas (II) and (III) are each a halogen group or hydrogen atom, unless all of $X_1$, $X_2$, $X_3$, $X_4$, $X_5$ and $X_6$ are each a halogen group, m is an integer of 2 or more, and m+n is an integer of 3 to 7.

In the chemical formula (I), it is preferable that $R_3$ and $R_4$ are each a hydrogen atom. It is also preferable that at least one of the combinations ($R_1$ and $R_2$) and ($R_3$ and $R_4$) forms a cyclic structure, after $R_1$ and $R_2$ or $R_3$ and $R_4$ are bound to each other. Moreover, $R_1$, $R_2$, $R_3$ and $R_4$ preferably have 1 to 15, more preferably 2 to 15, particularly preferably 2 to 6 carbon atoms, when they are functional groups. It is also preferable that an even number of Xs are each a halogen group, at least two of which are bound to the same acene ring. It is particularly preferable that two of Xs are each a halogen group bound to the same acene ring. Still more, k is preferably 1 or 2.

The hydroxypolyacene derivative of the present invention has a chemical structure corresponding to that of the polyacene, represented by the chemical formula (IV). It has the same number of 6-membered rings and the same $R_1$, $R_2$, $R_3$ and $R_4$, and has at least one carbon atom, except for the one to which $R_1$, $R_2$, $R_3$ or $R_4$ will bound when it is converted into the polyacene, bound to a hydroxyl group and hydrogen atom.

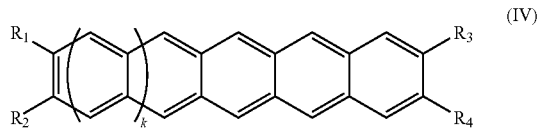

(IV)

In the chemical formula (IV), at least one of $R_1$, $R_2$, $R_3$ and $R_4$ is/are an aliphatic hydrocarbon group (such as an alkyl group, alkenyl group or alkynyl group), aryl group, alkoxy group, aryloxy group, acyl group, ester group, alkyloxycarbonyl group, aryloxycarbonyl group, carboxyl group, formyl group, hydroxyl group, halogen group, amino group, imino group, amide group, cyano group, silyl group, mercapto group, sulfide group, disulfide group or sulfonyl group, or a functional group containing 2 or more groups thereof, and the other(s) is/are a hydrogen atom. Moreover, k is an integer of 1 to 5.

The hydroxypolyacene derivative of the present invention has a chemical structure represented by the chemical formula (III).

Moreover, in the display device of the present invention, which is provided with pixel planes each composed of a number of pixels, each of the pixels is provided with the organic semiconductor device or transistor of the present invention as described above.

An electrode, dielectric layer and semiconductor layer are preferably formed in the organic semiconductor device or transistor by printing or coating of a liquid.

The polyacene compound of the present invention has a long and thin polyacene skeleton with functional groups at one or both ends of the major axis and with halogen groups on the sides. The inventors of the present invention have considered that a polyacene compound can have an increased solubility in solvents when substituted with functional groups at one or both end of the major axis and improved oxidation resistance when substituted with halogen groups on the sides, reaching the novel polyacene compound of the present invention, represented by the chemical formula (I).

They have found that the polyacene compound and thin film thereof of the present invention exhibit a mobility equivalent to or higher than that of pentacene, known to exhibit the highest mobility among the conventional organic materials. They also have found that the polyacene compound of the present invention is more soluble in solvents than pentacene, known to be soluble to a limited extent in solvents at normal temperature, that it has excellent oxidation resistance, and that the organic semiconductor device incorporated with the thin film of the polyacene compound of the present invention exhibits excellent electronic characteristics.

In short, the polyacene compound of the present invention exhibits a high mobility, solubility in solvents and oxidation resistance. The organic semiconductor thin film of the present invention exhibits a high mobility, and the organic semiconductor device of the present invention exhibits excellent electronic characteristics.

Moreover, the method for producing a polyacene compound of the present invention can easily produce the polyacene compound, described above.

BEST MODE FOR CARRYING OUT THE INVENTION

Figure 1:
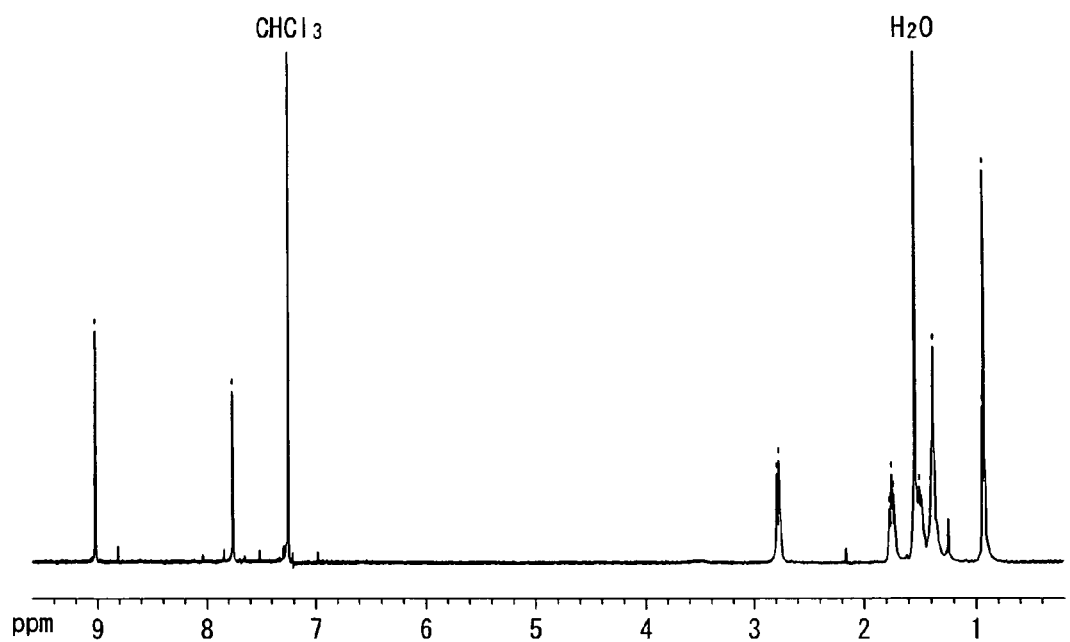
FIG. 1 shows a $^1$H-NMR spectrum of 6,13-dichloro-2,3,9,10-tetrahexylpentane.

The polyacene compound of the present invention has a structure represented by the chemical formula (I).

The functional groups $R_1$, $R_2$, $R_3$ and $R_4$ at the ends of the major axis are preferably each an aliphatic hydrocarbon group, e.g., alkyl, alkenyl or alkynyl group. They preferably have 1 to 15 carbon atoms in consideration of assuring solubility in solvents and crystallinity, more preferably 2 to 15 carbon atoms in consideration of assuring high solubility in solvents, and particularly preferably 2 to 6 carbon atoms in consideration of assuring both high solubility and high crystallinity. The hydrocarbon group may be structurally linear, branched or cyclic.

The alkyl groups include a methyl group, ethyl group, n-propyl group, n-butyl group, t-butyl group, n-hexyl group, dodecanyl group, trifluoromethyl group and benzyl group. The alkenyl groups include a methacryl group and acryl group. The alkynyl groups include an ethynyl group and propagyl group. The alkenyl and alkynyl groups may have the double or triple bond at any position in the functional group. The double or triple bond can be used to strengthen the functional group structure, to react the group with another molecule through the unsaturated bonding group, and to react (combine) or polymerize the unsaturated groups with each other.

Examples of suitable functional groups ($R_1$, $R_2$, $R_3$ and $R_4$), other than aliphatic hydrocarbon group, at the ends of the major axis are described. They preferably have 1 to 15, more preferably 2 to 15, and particularly preferably 2 to 6 carbon atoms, as is the case with the aliphatic hydrocarbon group described above. Aryloxy groups include a phenoxy group, naphthoxy group, phenylphenoxy group and 4-methylphenoxy group. Alkoxy groups include a methoxy group, ethoxy group, 2-methoxyethoxy group and t-butoxy group. Acyl groups include formyl group, acetyl group, 2-methylpropanoyl group, cyclohexylcarbonyl group, octanoyl group, 2-hexyldecanoyl group, dodecanoyl group, chloroacetyl group, trifluoroacetyl group and benzoyl group. Aryloxycarbonyl groups include phenoxycarbonyl group, 4-octyloxyphenoxycarbonyl group, 2-hydroxymethylphenoxycarbonyl group and 4-dodecyloxyphenoxycarbonyl group.

Amino groups include amino group, dimethylamino group, methylamino group, methylphenylamino group and phenylamino group. Sulfide and disulfide groups include all of those having a "—S—" or "—S—S—" partial structure. They may have a cyclic structure, e.g., a thiolane, 1,3-dithiolane, 1,2-dithiolane, thiane, dithiane or thiomorpholine ring. The cyclic structure is more preferable than the linear structure viewed from smaller steric effect. In particular, those functional groups having a five- or 6-membered ring are preferable for keeping planarity of the acene ring.

Silyl groups include a trimethylsilyl group, dimethylphenylsiloxy group and diphenylmethylsiloxy group. Sulfonyl groups include a methylsulfonyl group, n-butylsulfonyl group, n-octylsulfonyl group, n-butylsulfonyl group and phenylsulfonyl group.

All of the functional groups $R_1$, $R_2$, $R_3$ and $R_4$ may be different from each other, or they may be totally or partly identical. For example, all of $R_1$, $R_2$, $R_3$ and $R_4$ may be an alkyl group, or some may be an alkyl group and others may be hydrogen atom.

The functional groups at the major axis end(s) and sides of the polyacene skeleton in the pentacene compound may cause hindrance (steric hindrance) when the molecules are stacked on top of another to inhibit intermolecular overlapping on the conjugated planes. Therefore, the number of functional groups at the major axis end is preferably smaller. In particular, the polyacene structure with one or more functional groups at only one end is preferable in that the molecules are stacked in such a way that the ends with functional group(s) are directed to the opposite sides alternately. Moreover, the above structure is preferable also viewed from improved solubility in solvents, because of polarity evolving in the major axis direction of the molecules.

Moreover, $R_1$ and $R_2$ may be bound to each other to form a ring represented by the formula -A-$(CH_2)_n$-A- (where A is, for example, oxygen or sulfur atom, and "n" is an integer of 1 or more). It is needless to say that $R_1$ and $R_2$, and $R_3$ and $R_4$ are bound to each other simultaneously to form the above ring.

$R_1$, $R_2$, $R_3$ and $R_4$ at the major axis end(s) may be a composite group formed by combining two or more functional groups described above.

Some Xs are each a halogen group and others hydrogen atom. For example, one of Xs is a halogen group and others hydrogen atom, or one of them may be hydrogen atom and others a halogen group. When two or more Xs are each a halogen group, these halogens may be identical or different from each other. The case of all of Xs being each a halogen group is outside of the scope of the present invention.

The polyacene compound with an even number of Xs being each a halogen group and two of them bound to the same acene ring is preferable in that a polyacenequinone (which is a precursor for synthesis of polyacene compound) with two carbonyl groups in the same acene ring can be easily synthesized and extent of steric hindrance can be reduced between halogen groups when the molecules are stacked on top of another.

The functional groups at the major axis end(s) and sides of the polyacene skeleton in the pentacene compound may cause hindrance (steric hindrance) when the molecules are stacked on top of another to inhibit intermolecular overlapping on the conjugated planes. Therefore, the number of functional groups at the sides of the major axis is preferably smaller. The halogen group is preferably fluorine, because of its smallest van der Waals radius among halogen atoms.

For the number of condensed rings in the polyacene skeleton, k in the chemical formula (I) is preferably 1 or 2. The polyacene compound having a larger number of condensed rings generally has a lower solubility in solvents and increased reactivity with oxygen, i.e., decreased oxidation resistance. On the other hand, increasing number of condensed rings diminishes HOMO-LUMO gap, by which increased the value of mobility is expected. In consideration of solubility, stability and semiconductor characteristics, pentacene with k of 1 (i.e., condensed ring number of 5) and hexacene with k of 2 (i.e., condensed ring number of 6) are more preferable.

Next, the method for synthesizing the polyacene compound of the present invention is described. The polyacene compound of the present invention is a halogen-substituted polyacene derivative, which can be synthesized in two stages from a starting material of polyacenequinone compound having a chemical structure corresponding to that of the polyacene compound of the present invention. The polyacenequinone compound having a chemical structure corresponding to that of the polyacene compound shares the same number of 6-membered rings, and the same species, number and substitution positions of the functional groups with the polyacene compound. However, the polyacenequinone compound has carbonyl group, and a ring structure different from the polyacene structure.

The first stage reduces carbonyl group in the polyacenequinone compound with a metal hydride, e.g., lithium aluminum hydride, as a reducing agent into hydroxyl group. The reduction product (hydroxypolyacene derivative) is reacted with a halogenation agent, e.g., N-chlorosuccinimide, in the presence of dimethyl sulfide. This allows the halogen substitution and aromatization to proceed continuously to produce the halogen-substituted polyacene derivative.

In other words, a halogen group is introduced into the carbonyl carbon in the polyacenequinone compound, to form the halogen-substituted polyacene derivative. The number of quinone part(s) may be one or more. The polyacenequinone compound with a plurality of quinone parts can give the polyacene derivative substituted with a plurality of halogens. The hydroxypolyacene derivative has a chemical structure corresponding to that of the polyacene compound, sharing the same number of 6-membered rings, and the same species, number and substitution positions of the functional groups with the polyacene compound. However, the hydroxypolyacene derivative has a carbon atom bound to hydroxyl group and hydrogen atom, and has a ring structure different from the polyacene structure.

For example, a 6,13-dihalogenated pentacene derivative can be synthesized from a 6,13-pentacenequinone derivative in two stages. For example, a 6,13-pentacenequinone derivative having substituents at both ends of the major axis can be easily produced by cyclization/condensation between a phthalaldehyde derivative and cyclohexane-1,4-dione. On the other hand, a 6,13-pentacenequinone derivative having substituent(s) at one end of the major axis can be easily produced by cyclization/condensation between a phthalaldehyde derivative and 1,4-dihydroxyanthracene.

A 6,13-pentacenequinone derivative substituted at one or both ends of the major axis can be converted into a 6,13-dihalogenated pentacene derivative having substituent(s) at one or both ends by the reduction and halogenation/aromatization, described above. The polyacene compound of the present invention can be synthesized in a manner similar to the above, and the desired polyacene compound halogenated at a plurality of positions can be efficiently produced.

The polyacene compound of the present invention exhibits crystallinity, the crystal structure having molecules arranged in a herring-bone pattern. This crystal structure takes a lattice structure with long and thin molecules being stacked in a nock pattern. The crystal structure can be determined by X-ray diffractometry.

Moreover, the polyacene compound of the present invention exhibits an orthorhombic or cubic structure like an unsubstituted polyacene compound. The crystal lattice constants a, b, and c can be determined, where the c-axis constant corresponds to a lattice unit length of long and thin molecules arranged, whereas the a-axis and b-axis constants correspond to magnitude of the lattice unit on the molecular column plane on which the molecule conjugated plane is stacked.

Moreover, the polyacene compound of the present invention has an intermolecular distance on the plane on which the molecule conjugated plane is stacked (corresponding to the a-axis and b-axis constants) equivalent to or shorter than that of an unsubstituted polyacene compound. This means that more π-electrons overlap each other between the molecules, facilitating carrier movement between the molecules. This conceivably accounts for a higher mobility in the polyacene compound. The c-axis constant changes with molecular length of the polyacene compound in the major axis direction, and is almost equivalent to or slightly shorter than the molecular length.

Moreover, the polyacene compound of the present invention, having halogen atoms in the molecular structure, is more resistant to oxidation than a halogen-free structure, because halogen atoms introduced increase ionization potential of the molecule to decrease its reactivity with an oxidant, e.g., oxygen. Halogen atoms introduced also control charge transfer with an electron accepting molecule, leading to increased stability to semiconductor carrier concentration changes. Still more, the polyacene compound of the present invention, when applied to a field-effect transistor, changes drain current more for a gate voltage, creating higher on/off current ratio.

Next, the organic semiconductor thin film of the present invention is described.

The organic semiconductor thin film of the present invention can be formed on a substrate by a known method, e.g., vacuum deposition, molecular beam epitaxy (MBE), sputtering, laser deposition or vapor-phase transfer/growth.

The polyacene compound for the present invention sublimates, and can be formed into a thin film by one of the methods described above. MBE, vacuum deposition and vapor-phase transfer/growth heat the polyacene compound and transfer, under a vacuum of varying degree (e.g. high vacuum, low vacuum) or normal pressure, the sublimated vapor onto a substrate on which the thin polyacene film is formed. Sputtering ionizes the polyacene compound in a plasma and deposits the ionized molecules on a substrate to form a thin film thereon. Laser deposition heats the polyacene compound by irradiation with laser beams and deposits the resulting vapor molecules on a substrate to form a thin film thereon. Of these methods, MBE, vacuum deposition and vapor-phase transfer/growth are more preferable viewed from higher flatness and crystallinity of the film they form.

For the film-making conditions, substrate temperature, for example, is preferably room temperature to 100° C. for MBE or vacuum deposition. A thin film tends to be amorphous when formed on a substrate kept at a lower temperature, and have deteriorated surface flatness/smoothness on a substrate kept at above 100° C. It is preferably room temperature to 200° C. for vapor-phase transfer/growth.

The polyacene compound of the present invention can be formed into a thin film of high crystallinity even at a high film growth rate. In other words, it can be treated by a high-speed film-making process. Growth rate is preferably in a range from 0.1 nm/minute to 1 µm/second. At below 0.1 nm/minute, the thin film may easily reduce crystallinity. At above 1 µm/second, it may have deteriorated surface flatness/smoothness.

The organic semiconductor thin film of the present invention can be formed also by a wet process. A known unsubstituted polyacene compound is generally sparingly soluble in solvents at room temperature, making it difficult to prepare the solution and to spread the solution to form a thin film. On the other hand, the polyacene compound of the present invention is comparable to an unsubstituted polyacene compound in solubility in solvents by virtue of the functional groups introduced. Therefore, it can be dissolved in a solvent at room temperature and the resulting solution can be spread on a substrate to form a thin film thereon. The suitable solvents for preparing the solution include hexane, pentane, xylene, toluene, tetrahydrofuran, chloroform, dichloromethane, dichloroethane, 1,1,2,2-tetrachloroethane, dichlorobenzene and trichlorobenzene. They may be used either individually or in combination of two or more kinds.

The organic semiconductor thin film of the present invention can be produced by spreading a solution of the polyacene compound of the present invention on a base, e.g., substrate, and vaporizing the solvent by an adequate method, e.g., heating. The solution can be spread on a base by coating, spraying or by another method for bringing the base into contact with the solution. More specifically, these methods include spin coating, dip coating, screen printing, ink jet printing, blade coating, printing (planography, relief or intaglio printing), which are known. Species of solvent and polyacene compound concentration to be used vary depending on the printing method adopted. It is therefore preferable to prepare the solution suitable for the printing method adopted.

The above process may be carried out in the normal atmosphere or an inert gas atmosphere, e.g., of nitrogen or argon. The crystal growth can be controlled by adjusting solvent vaporization rate in the vapor-liquid interface based on temperature in the vicinity of the base and/or solvent vapor pressure in the atmosphere.

It is preferable to diminish the residual solvent in the organic semiconductor thin film as far as possible, viewed from stability and semiconductor characteristics of the film. Therefore, it is preferable to remove the residual solvent almost completely by further treating the thin film formed on the base under heating or under a vacuum.

Thus, the organic semiconductor thin film of the polyacene compound can be produced either by a dry or wet process.

As discussed above, the polyacene compound of the present invention can give a thin film of excellent crystallinity and semiconductor characteristics. The polyacene compound has the major axis oriented toward a right angle to the base plane in the organic semiconductor thin film of the present invention, conceivably on account of high molecular cohesion of the compound to easily form the molecular column with the molecules stacked on top of another on the molecular planes. As a result, intensity on the crystal (00n) plane is more notably expressed in an X-ray diffraction pattern of the thin film. The interplanar distance corresponds to the c-axis lattice constant of the crystal.

The polyacene compound of the present invention may have a shortened intermolecular distance in the a- and/or b-crystallographic axes direction, the shortened distance facilitating carrier movement to increase mobility of the compound. The organic semiconductor device which uses the organic semiconductor thin film is considered to facilitate carrier movement along the molecular columns arranged in layers. The a- and b-axis lattice constants can be observed by an adequate method, e.g., X-ray diffractometry with ray injected at an angle, transmission electron beam diffractometry or diffractometry with X-ray injected onto the thin film edges.

A common inorganic semiconductor thin film has crystallinity amenable to crystallinity and plane orientation of a base on which it is formed. By contrast, the organic semiconductor thin film of the present invention exhibits high crystallinity irrespective of base crystallinity and plane orientation. Therefore, the base material can be selected from widely varying materials, whether they are crystalline or amorphous.

The useful base materials include ceramics, e.g., glass, quartz, aluminum oxide, sapphire, silicon nitride and silicon carbide; semiconductors, e.g., silicon, germanium, gallium arsenide, gallium phosphide and gallium nitride; resins, e.g., polyesters (e.g., polyethylene terephthalate and polyethylene naphthalate), polyethylene, polypropylene, polyvinyl alcohol, ethylene/vinyl alcohol copolymer, cyclic polyolefin, polyimide, polyamide, polystyrene, polycarbonate, polyethersulfone, polysulfone and polymethyl methacrylate; and paper and non-woven fabric.

The base is not limited in shape. However, it is normally sheet- or plate-shaped.

The organic semiconductor thin film of the present invention has a high carrier mobility, which is one of its major advantages. Mobility is preferably $1\times10^{-4}$ cm$^2$/V·s or more, more preferably $1\times10^{-3}$ cm$^2$/V·s or more, and most preferably $1\times10^{-2}$ cm$^2$/V·s or more.

The organic semiconductor thin film can make semiconductor devices useful in various areas, e.g., electronics, photonics and bioelectronics. Examples of the semiconductor devices include diode, transistor, thin-film transistor, memory, photodiode, light-emitting diode, light-emitting transistor and sensor.

The transistor and thin-film transistor can be used for various displays, e.g., liquid crystal display, dispersed liquid crystal display, electrophoretic display, particle rotating display, electrochromic display, organic light-emitting display, electronic paper and so forth. The transistor and thin-film transistor are used for various devices, e.g., pixel switching transistor, signal driving circuit, memory circuit, signal processing circuit and so forth in these displays.

When the semiconductor device is a transistor, it may take various structures, e.g., substrate/gate electrode/insulation layer (dielectric layer)/source and drain electrodes/semiconductor layer, substrate/semiconductor layer/source and drain electrodes/insulation layer (dielectric layer)/gate electrode, substrate/source or drain electrode/semiconductor layer+insulation layer (dielectric layer)+gate electrode/drain or source electrode, where a plurality of source, drain or gate electrodes may be used. Moreover, a plurality of semiconductor layers may be used, on the same plane or stacked on top of another.

The transistor may have an MOS (metal-oxide (insulation layer)-semiconductor) or bipolar structure. The polyacene compound is normally a p-type semiconductor, and may be combined with another species of the polyacene compound doped with a donor to be of n-type, or with an n-type semiconductor other than the polyacene compound, to form a device.

When the semiconductor device is a diode, it may take an electrode/n-type semiconductor/p-type semiconductor/electrode structure, where the organic semiconductor thin film of the present invention is used as the p-type semiconductor and the n-type semiconductor described above is used as the n-type semiconductor.

A Schottky junction and/or tunnel junction may be used in the semiconductor device in the organic semiconductor thin film or at a joint between the thin film surface and electrode, at least partly. The semiconductor device having the above junction structure is preferable, because it can make a diode or transistor by a simple structure. A plurality of the organic semiconductor devices having the above junction structure may be combined with each other to form various devices, e.g., inverter, oscillator, memory and sensor.

When the semiconductor device of the present invention is used for a display device, it can work as a transistor device (display TFT) for switching each pixel after being set at each pixel of the display device. Such an active driving display device, needing no patterning of an electroconductive substrate which it faces, can simplify pixel interconnections as compared with a passive driving display device, which has no transistor for pixel switching, depending on circuit structure. Generally, one to several switching transistors are allocated to each pixel. Such a display device has a structure with data lines and gate lines arranged two-dimensionally on a substrate to intersect with each other, where each of the data and gate lines is connected to a transistor gate, source and drain electrodes. It is possible to separate the data and gate lines from each other, and add current supply lines and/or signal lines.

A pixel of the display device can be provided with a capacitor in addition to pixel interconnections and transistor to have a signal recording function. Moreover, a substrate on which display devices are formed can be further provided with a data line and gate line drivers, pixel signal memory, pulse generator, signal splitter, controller and so forth.

Moreover, the organic semiconductor device of the present invention may be used as an arithmetic or memory device for an IC card, smart card and electronic tag. It is applicable to these devices without causing any problem, whether they are of contact or non-contact type. These devices are composed of a memory, pulse generator, signal splitter, controller, capacitor and so forth, and may be further provided with an antenna and/or battery.

The organic semiconductor device of the present invention, when used for a diode, device having a Schottky junction structure and device having a tunnel junction structure, can work as a light-receiving device or photodiode for a photoelectric converter, photovoltaic cell or infrared sensor, or as a light-emitting device. When it is used for a transistor, the transistor can work as a light-emitting transistor. The light-emitting layer for these light-emitting devices may be made of a known organic or inorganic material.

The organic semiconductor device of the present invention can be also used for a variety of sensors, e.g., gas sensor, biosensor, blood sensor, immunization sensor, artificial retina, taste sensor and so forth. Generally, the organic semiconductor thin film for the organic semiconductor device analyzes an object to be measured by change in resistance values of the thin film evolving when it is brought into contact with or close to the object.

The present invention is described in more detail by EXAMPLES.

EXAMPLE 1

Synthesis of 6,13-dichloro-2,3,9,10-tetrahexylpentacene

<Synthesis of Intermediate>

A solution of 649 mg of 2,3,9,10-tetrahexyl-6,13-pentacenequinone dissolved in 30 mL of tetrahydrofuran (THF) was added to 5 mL of a 1 mol/1000 mL THF solution of lithium triethylborohydride, and the mixture was heated for 12 hours under reflux in a nitrogen atmosphere. The resulting solution was neutralized with diluted aqueous hydrochloric acid, and the organic phase was separated, concentrated and dried under a vacuum to produce 2,3,9,10-tetrahexyl-6,13-dihydro-6,13-dihydroxypentacene almost stoichiometrically (see the following reaction formula).

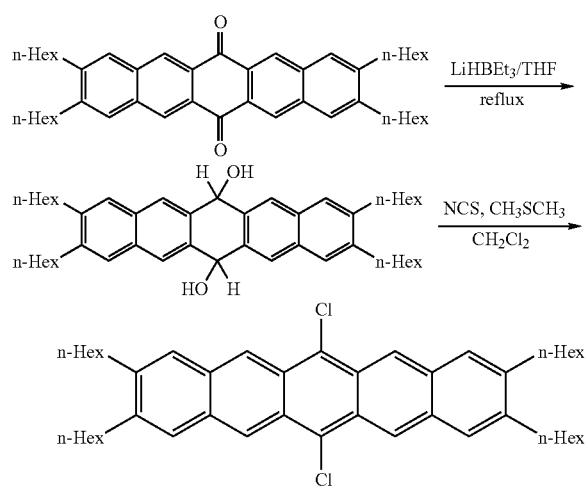

The resulting 2,3,9,10-tetrahexyl-6,13-dihydro-6,13-dihydroxypentacene was analyzed by mass spectrometry. The results are given below.

FAB-MS(NBA): m/z=649

Moreover, it was analyzed by nuclear magnetic resonance spectroscopy (NMR) at room temperature with deuterated chloroform as a solvent. The results are given below.

$^1$H-NMR (ppm): δ0.88-0.91 (m, 12H), 1.32-1.35 (m, 16H), 1.48-1.52 (m, 8H), 1.63-1.67 (m, 8H), 2.75 (t, 8H), 5.74 (s, 2H), 7.58 (s, 4H), 7.80 (s, 4H)

<Method for Producing Polyacene Compound>

N-chlorosuccinimide (382 mg) was dissolved in 40 mL of dichloromethane in a nitrogen atmosphere, and the resulting solution was cooled to −20° C., added to 0.32 mL of dimethyl sulfide dropwise, and stirred for 10 minutes. Then, the resulting solution was added to a solution of 231 mg of 2,3,9,10-tetrahexyl-6,13-dihydro-6,13-dihydroxypentacene dissolved in 20 mL of dichloromethane dropwise, and then the reaction was carried out for 18 hours while being warmed up to room temperature (see the above reaction formula).

The reaction system was added to water to terminate the reaction. The reaction product was extracted with chloroform, and the organic phase separated was washed with a saturated NaCl aqueous solution and dried with magnesium sulfate. The organic phase was distilled under a vacuum to remove the organic solvent, and the resulting residue was reprecipitated in a mixed solvent of benzene and n-hexane. This produced 74 mg of pure 6,13-dichloro-2,3,9,10-tetrahexylpentacene in a yield of 30%.

The resulting 6,13-dichloro-2,3,9,10-tetrahexylpentacene was analyzed by mass spectrometry. The results are given below.

FAB-MS(NBA): m/z=684, 682

Moreover, it was analyzed by nuclear magnetic resonance spectroscopy (NMR) at room temperature with deuterated chloroform as a solvent. The results are given below, and also in FIG. 1, which presents a chart.

$^1$H-NMR (ppm): δ0.90-0.93 (m, 12H), 1.35-1.39 (m, 16H), 1.48-1.50 (m, 8H), 1.71-1.80 (m, 8H), 2.77 (t, 8H), 7.76 (s, 4H), 9.01 (s, 4H)

<Method for Producing Organic Semiconductor Thin Film>

The 6,13-dichloro-2,3,9,10-tetrahexylpentacene synthesized above was dissolved in chloroform in a nitrogen atmosphere, to produce a bluish purple solution (concentration: 0.2% by mass). The solution was spread on a silicon substrate by spin coating (rotational speed: 2,000 rpm, rotation time: 20 seconds) in a nitrogen atmosphere to form a 120 nm thick thin film of 6,13-dichloro-2,3,9,10-tetrahexylpentacene.

Figure 2:
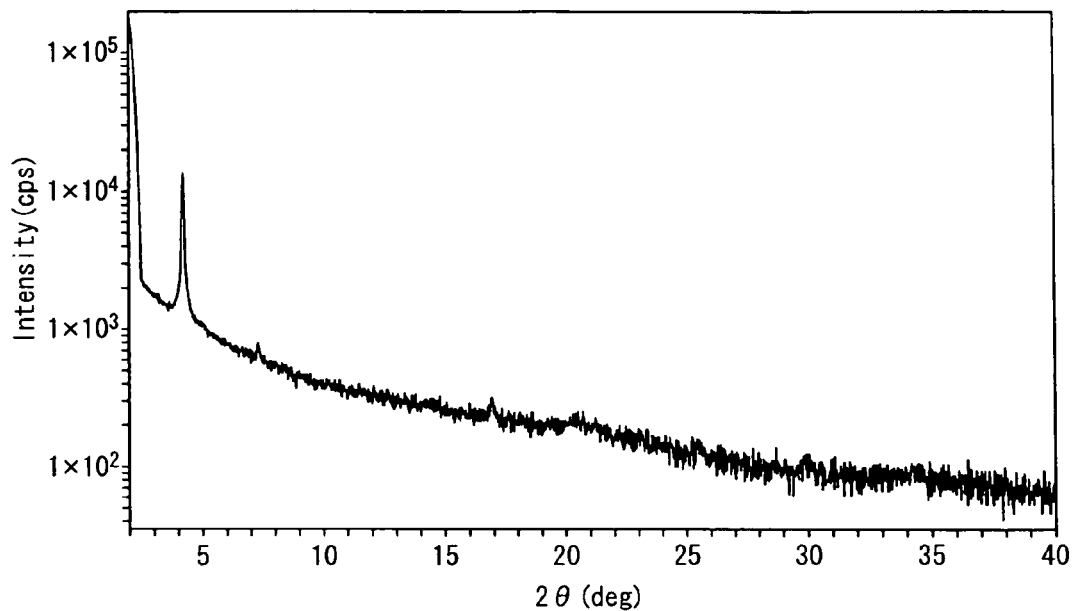
FIG. 2 shows an X-ray diffraction pattern of a thin film of 6,13-dichloro-2,3,9,10-tetrahexylpentane.

The thin film of 6,13-dichloro-2,3,9,10-tetrahexylpentacene, prepared above, was analyzed by wide-angle X-ray diffraction analysis. The results are given in FIG. 2, which presents a diffraction pattern chart. As shown, the diffraction lines relevant to the (00n) plane (n=1, 2, 3 and 4) were observed, and the crystal lattice constant of the thin film was found to be 4.2 nm from the interplanar distance. Given that the 6,13-dichloro-2,3,9,10-tetrahexylpentacene molecule is 4.0 to 4.2 nm long in the major axis direction, it was found that the molecules formed the crystal in the thin film with the major axes of molecule being oriented toward a right angle to the substrate surface.

<Organic Semiconductor Device>

A silicon substrate (coated with a 200 nm thick thermally oxidized layer), heavily doped with an n-type dopant, was formed with a pattern of gold working as a source and drain electrodes. The gold electrode pattern comprises strips running in parallel to each other, spaced from each other by 20 μm (channel length). The pattern is 500 μm long (channel width).

The silicon substrate with the patterned electrodes was coated with a thin film of 6,13-dichloro-2,3,9,10-tetrahexylpentacene by spin coating, similar to the above, to form a transistor structure.

Figure 3:
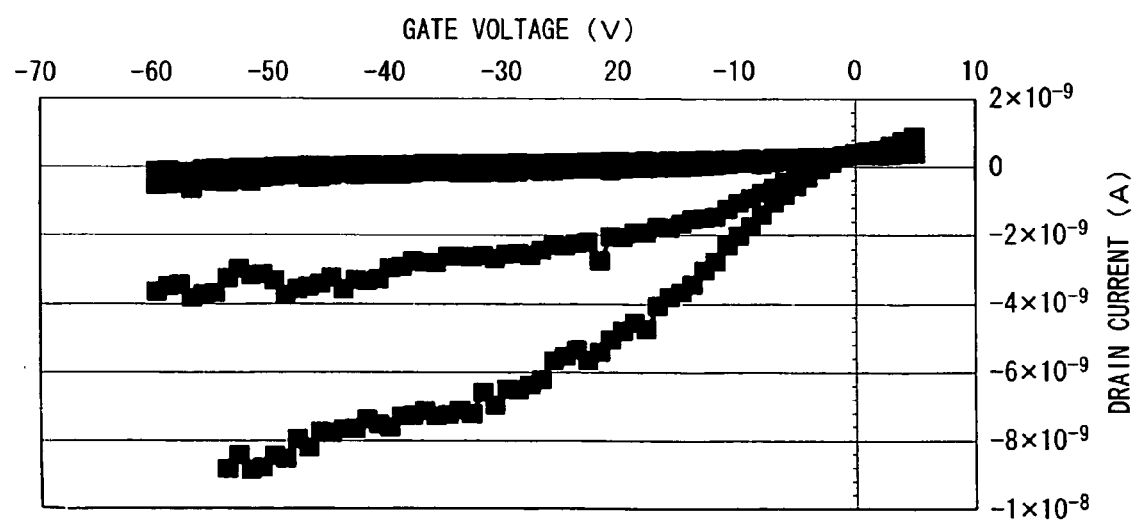
FIG. 3 shows a drain current/drain voltage curve of the transistor prepared in EXAMPLE 1.

The transistor was analyzed for current/voltage curve between the source and drain electrodes with the silicon substrate as the gate, where the gate voltage was changed at 10 V intervals from −10 to −40 V. It was observed that the drain current was saturated as the drain voltage increased, as shown in FIG. 3. Mobility determined from gate voltage dependence in the current saturated region was $5\times10^{-3}$ cm$^2$/V·s.

EXAMPLE 2

Synthesis of 6,13-dichloro-2,3,9,10-tetrapropylpentacene

<Synthesis of Intermediate>

A solution of 357 mg of 2,3,9,10-tetrapropyl-6,13-pentacenequinone dissolved in 50 mL of THF was added to 11 mL of a 1 mol/1000 mL THF solution of lithium triethylborohydride, and the mixture was heated for 24 hours under reflux in a nitrogen atmosphere. The resulting solution was neutralized with diluted aqueous hydrochloric acid, and the organic phase was separated, concentrated and dried under a vacuum to produce 6,13-dihydro-6,13-dihydroxy-2,3,9,10-tetrapropylpentacene almost stoichiometrically.

The resulting 6,13-dihydro-6,13-dihydroxy-2,3,9,10-tetrapropylpentacene was analyzed by nuclear magnetic resonance spectroscopy (NMR) at room temperature with deuterated chloroform as a solvent. The results are given below.

$^1$H-NMR (ppm): δ1.05 (t, 12H), 1.67-1.77 (m, 8H), 2.76 (t, 8H), 5.78 (s, 2H), 7.61 (s, 4H), 7.81 (s, 4H)

<Method for Producing Polyacene Compound>

N-chlorosuccinimide (800 mg) was dissolved in 45 mL of dichloromethane in a nitrogen atmosphere, and the resulting solution was cooled to −20° C., added to 0.66 mL of dimethyl sulfide dropwise, and stirred for 10 minutes. Then, the resulting solution was added to a solution of 361 mg of 6,13-dihydro-6,13-dihydroxy-2,3,9,10-tetrapropylpentacene dissolved in 35 mL of dichloromethane dropwise, and then the reaction was carried out for 18 hours while being warmed up to room temperature.

The reaction system was added to water to terminate the reaction. The reaction product was extracted with chloroform, and the organic phase separated was washed with a saturated NaCl aqueous solution and dried with magnesium sulfate. The organic phase was distilled under a vacuum to remove the organic solvent, and the resulting residue was reprecipitated in benzene. This produced 38 mg of pure 6,13-dichloro-2,3,9,10-tetrapropylpentacene in a yield of 10%.

The resulting 6,13-dichloro-2,3,9,10-tetrapropylpentacene was analyzed by mass spectrometry. The results are given below.

FAB-HRMS (NBA): m/z=514.2208 (calculated value: 514.2194)

Moreover, it was analyzed by nuclear magnetic resonance spectroscopy (NMR) at room temperature with deuterated chloroform as a solvent. The results are given below.

$^1$H-NMR (ppm): δ1.08 (t, 12H), 1.73-1.82 (m, 8H), 2.76 (t, 8H), 7.76 (s, 4H), 9.01 (s, 4H)

<Method for Producing Organic Semiconductor Thin Film>

The 6,13-dichloro-2,3,9,10-tetrapropylpentacene synthesized above was dissolved in toluene in a nitrogen atmosphere, to produce a bluish purple solution (concentration: 0.2% by mass). The solution was spread on a silicon substrate by spin coating (rotational speed: 1,000 rpm, rotation time: 10 seconds) in a nitrogen atmosphere to form a 120 nm thick thin film of 6,13-dichloro-2,3,9,10-tetrapropylpentacene.

The thin film of 6,13-dichloro-2,3,9,10-tetrapropylpentacene, prepared above, was analyzed by wide-angle X-ray diffraction analysis. The diffraction lines relevant to the (00n) plane (n=3, 4, 5 and 6) were observed, and the crystal lattice constant of the thin film was found to be 4.3 nm from the interplanar distance. Given that the 6,13-dichloro-2,3,9,10-tetrapropylpentacene molecule is 2.2 to 2.4 nm long in the major axis direction, it was found that the molecules formed the crystal in the thin film with the major axes of molecule being oriented toward a right angle to the substrate surface.

<Organic Semiconductor Device>

A silicon substrate (coated with a 200 nm thick thermally oxidized layer), heavily doped with an n-type dopant, was formed with a pattern of gold working as a source and drain electrodes. The gold electrode pattern comprises strips running in parallel to each other, spaced from each other by 50 μm (channel length). The pattern was 500 μm long (channel width).

The silicon substrate with the patterned electrodes was coated with a thin film of 6,13-dichloro-2,3,9,10-tetrapropylpentacene by spin coating, similar to the above, to form a transistor structure.

The transistor was analyzed for current/voltage curve between the source and drain electrodes with the silicon substrate as the gate, where the gate voltage was changed at 10 V intervals from −10 to −40 V. It was observed that the drain current was saturated as the drain voltage increased. Mobility determined from gate voltage dependence in the current saturated region was $5 \times 10^{-2}$ cm$^2$/V·s.

EXAMPLE 3

Synthesis of 6,13-dichloro-2,3-dipropylpentacene

<Synthesis of Intermediate>

A solution of 314 mg of 2,3-dipropyl-6,13-pentacenequinone dissolved in 60 mL of THF was added to 6 mL of a 1 mol/1000 mL THF solution of lithium triethylborohydride, and the mixture was heated for 20 hours under reflux in a nitrogen atmosphere. The resulting solution was neutralized with diluted aqueous hydrochloric acid, and the organic phase was separated, concentrated and dried under a vacuum to produce 6,13-dihydro-6,13-dihydroxy-2,3-dipropylpentacene almost stoichiometrically.

<Method for Producing Polyacene Compound>

N-chlorosuccinimide (1.0 g) was dissolved in 60 mL of dichloromethane in a nitrogen atmosphere, and the resulting solution was cooled to −20° C., added to 0.83 mL of dimethyl sulfide dropwise, and stirred for 10 minutes. Then, the resulting solution was added to a solution of 317 mg of 6,13-dihydro-6,13-dihydroxy-2,3-dipropylpentacene dissolved in 50 mL of dichloromethane dropwise, and then the reaction was carried out for 18 hours while being warmed up to room temperature.

The reaction system was added to water to terminate the reaction. The reaction product was extracted with chloroform, and the organic phase separated was washed with a saturated NaCl aqueous solution and dried with magnesium sulfate. The organic phase was distilled under a vacuum to remove the organic solvent, and the resulting residue was reprecipitated in ethanol. This produced 17 mg of pure 6,13-dichloro-2,3-dipropylpentacene in a yield of 5%.

The resulting 6,13-dichloro-2,3-dipropylpentacene was analyzed by mass spectrometry. The results are given below.

FAB-MS(NBA): m/z=430.1258 (calculated value: 430.1255)

Moreover, it was analyzed by nuclear magnetic resonance spectroscopy (NMR) at room temperature with deuterated chloroform as a solvent. The results are given below.

$^1$H-NMR (ppm): δ1.08 (t, 6H), 1.73-1.82 (m, 4H), 2.75 (t, 4H), 7.38 (dd, 2H), 7.75 (s, 2H), 7.99 (dd, 2H), 9.00 (s, 2H), 9.11 (s, 2H)

<Method for Producing Organic Semiconductor Thin Film>

The 6,13-dichloro-2,3-dipropylpentacene synthesized above was dissolved in toluene in a nitrogen atmosphere, to produce a bluish purple solution (concentration: 0.2% by mass). The solution was spread on a silicon substrate by spin coating (rotational speed: 1,000 rpm, rotation time: 10 seconds) in a nitrogen atmosphere to form an 80 nm thick thin film of 6,13-dichloro-2,3-dipropylpentacene.

The thin film of 6,13-dichloro-2,3-dipropylpentacene, prepared above, was analyzed by wide-angle X-ray diffraction analysis. The diffraction lines relevant to the (00n) plane (n=1, 2, 3 and 4) were observed, and the crystal lattice constant of the thin film was found to be 2.4 nm from the interplanar distance. Given that the 6,13-dichloro-2,3-dipropylpentacene molecule is 2.0 to 2.4 nm long in the major axis direction, it was found that the molecules formed the crystal in the thin film with the major axes of molecule being oriented toward a right angle to the substrate surface.

<Organic Semiconductor Device>

A silicon substrate (coated with a 200 nm thick thermally oxidized layer), heavily doped with an n-type dopant, was formed with a pattern of gold working as a source and drain electrodes. The gold electrode pattern comprises strips running in parallel to each other, spaced from each other by 50 μm (channel length). The pattern is 500 μm long (channel width).

The silicon substrate with the patterned electrodes was coated with a thin film of 6,13-dichloro-2,3-dipropylpentacene by spin coating, similar to the above, to form a transistor structure.

The transistor was analyzed for current/voltage curve between the source and drain electrodes with the silicon substrate as the gate, where the gate voltage was changed at 10 V intervals from −10 to −40 V. It was observed that the drain current was saturated as the drain voltage increased. Mobility determined from gate voltage dependence in the current saturated region was 0.10 cm$^2$/V·s.

EXAMPLE 4

Synthesis of 6,13-dichloro-2,3-dihexylpentacene

<Synthesis of Intermediate>

A solution of 334 mg of 2,3-dihexyl-6,13-pentacenequinone dissolved in 50 mL of THF was added to 11 mL of a 1 mol/1000 mL THF solution of lithium triethylborohydride, and the mixture was heated for 20 hours under reflux in a nitrogen atmosphere. The resulting solution was neutralized with diluted aqueous hydrochloric acid, and the organic phase was separated, concentrated and dried under a vacuum to produce 2,3-dihexyl-6,13-dihydro-6,13-dihydroxypentacene almost stoichiometrically.

<Method for Producing Polyacene Compound>

N-chlorosuccinimide (780 mg) was dissolved in 40 mL of dichloromethane in a nitrogen atmosphere, and the resulting solution was cooled to −20° C., added to 0.64 mL of dimethyl sulfide dropwise, and stirred for 10 minutes. Then, the resulting solution was added to a solution of 336 mg of 2,3-dihexyl-6,13-dihydro-6,13-dihydroxypentacene dissolved in 40 mL of dichloromethane dropwise, and then the reaction was carried out for 18 hours while being warmed up to room temperature.

The reaction system was added to water to terminate the reaction. There action product was extracted with chloroform, and the organic phase separated was washed with a saturated NaCl aqueous solution and dried with magnesium sulfate. The organic phase was distilled under a vacuum to remove the organic solvent, and the resulting residue was reprecipitated in ethanol. This produced 35 mg of pure 6,13-dichloro-2,3-dihexylpentacene in a yield of 10%.

The resulting 6,13-dichloro-2,3-dihexylpentacene was analyzed by mass spectrometry. The results are given below.

FAB-HRMS (NBA): m/z=514.2193 (calculated value: 514.2194)

Moreover, it was analyzed by nuclear magnetic resonance spectroscopy (NMR) at room temperature with deuterated chloroform as a solvent. The results are given below.

$^1$H-NMR (ppm): δ0.92 (t, 6H) 1.30-1.50 (m, 12H), 1.68-1.76 (m, 4H), 2.74 (t, 4H), 7.37 (dd, 2H), 7.71 (s, 2H), 7.98 (dd, 2H), 8.96 (s, 2H), 9.08 (s, 2H)

<Method for Producing Organic Semiconductor Thin Film>

The 6,13-dichloro-2,3-dihexylpentacene synthesized above was dissolved in toluene in a nitrogen atmosphere, to produce a bluish purple solution (concentration: 0.2% by mass). The solution was spread on a silicon substrate by spin coating (rotational speed: 1,000 rpm, rotation time: 10 seconds) in a nitrogen atmosphere to form a 100 nm thick thin film of 6,13-dichloro-2,3-dihexylpentacene.

The thin film of 6,13-dichloro-2,3-dihexylpentacene, prepared above, was analyzed by wide-angle X-ray diffraction analysis. The diffraction lines relevant to the (00n) plane (n=1, 2, 3 and 4) were observed, and the crystal lattice constant of the thin film was found to be 1.1 nm from the interplanar distance. Given that the 6,13-dichloro-2,3-dihexylpentacene molecule is 2.2 to 2.5 nm long in the major axis direction, it is estimated that the molecules form the crystal in the thin film with the major axes of molecule being oriented toward a right angle to the substrate surface.

<Organic Semiconductor Device>

A silicon substrate (coated with a 200 nm thick thermally oxidized layer), heavily doped with an n-type dopant, was formed with a pattern of gold working as a source and drain electrodes. The gold electrode pattern comprises strips running in parallel to each other, spaced from each other by 50 μm (channel length). The pattern is 500 μm long (channel width).

The silicon substrate with the patterned electrodes was coated with a thin film of 6,13-dichloro-2,3-dihexylpentacene by spin coating, similar to the above, to form a transistor structure.

The transistor was analyzed for current/voltage curves between the source and drain electrodes with the substrate as the gate, where the gate voltage was changed at 10 V intervals from −10 to −40 V. It was observed that the drain current was saturated as the drain voltage increased. Mobility determined from gate voltage dependence in the current saturated region was $9 \times 10^{-3}$ cm$^2$/V·s.

EXAMPLE 5

Synthesis of 6,13-dibromo-2,3,9,10-tetrahexylpentacene

<Synthesis of Intermediate>

2,3,9,10-tetrahexyl-6,13-dihydro-6,13-dihydroxypenta cene was prepared in the same manner as in EXAMPLE 1.

<Method for Producing Polyacene Compound>

N-bromosuccinimide (338 mg) was dissolved in 20 mL of THF in a nitrogen atmosphere, and the resulting solution was cooled to −20° C., added to 0.20 mL of dimethyl sulfide dropwise, and stirred for 10 minutes. Then, the solution was added to a solution of 150 mg of 2,3,9,10-tetrahexyl-6,13-dihydro-6,13-dihydroxypentacene dissolved in 10 mL of THF dropwise, and then the reaction was carried out for 18 hours while being warmed up to room temperature.

The reaction system was added to water to terminate the reaction. The reaction product was extracted with chloroform, and the organic phase separated was washed with a saturated NaCl aqueous solution and dried with magnesium sulfate. The organic phase was distilled under a vacuum to remove the organic solvent, and the resulting residue was purified by silica gel column chromatography (solvent: mixture of benzene and hexane) This produced 30 mg of pure 6,13-dibromo-2,3,9,10-tetrahexylpentacene in a yield of 17%.

The resulting 6,13-dibromo-2,3,9,10-tetrahexylpentacene was analyzed by mass spectrometry. The results are given below.

FAB-MS(NBA): m/z=774, 772, 770

Moreover, it was analyzed by nuclear magnetic resonance spectroscopy (NMR) at room temperature with deuterated chloroform as a solvent. The results are given below.

$^1$H-NMR (ppm): δ0.92 (t, 12H), 1.30-1.53 (m, 24H), 1.68-1.78 (m, 8H), 2.77 (t, 8H), 7.77 (s, 4H), 9.05 (s, 4H)

<Method for Producing Organic Semiconductor Thin Film>

The 6,13-dibromo-2,3,9,10-tetrahexylpentacene synthesized above was dissolved in chloroform in a nitrogen atmosphere, to produce a bluish purple solution (concentration: 0.2% by mass). The solution was spread on a silicon substrate by spin coating (rotational speed: 1,000 rpm, rotation time: 10 seconds) in a nitrogen atmosphere to form a 120 nm thick thin film of 6,13-dibromo-2,3,9,10-tetrahexylpentacene.

The thin film of 6,13-dibromo-2,3,9,10-tetrahexylpentacene, prepared above, was analyzed by wide-angle X-ray diffraction analysis. The diffraction lines relevant to the (00n) plane (n=1, 2, 3 and 4) were observed, and the interplanar distance was found to be 2.2 nm. Given that the 6,13-dibromo-2,3,9,10-tetrahexylpentacene molecule is 2.3 to 2.7 nm long in the major axis direction, it was found that the molecules form the crystal in the thin film with the major axes of molecule being slightly slanted from a right angle to the substrate surface.

<Organic Semiconductor Device>

A silicon substrate (coated with a 200 nm thick thermally oxidized layer), heavily doped with an n-type dopant, was formed with a pattern of gold working as a source and drain electrodes. The gold electrode pattern comprises strips running in parallel to each other, spaced from each other by 50 μm (channel length). The pattern is 500 μm long (channel width).

The silicon substrate with the patterned electrodes was coated with a thin film of 6,13-dibromo-2,3,9,10-tetrahexylpentacene by spin coating, similar to the above, to form a transistor structure.

The transistor was analyzed for current/voltage curve between the source and drain electrodes with the silicon substrate as the gate, where the gate voltage was changed at 10 V intervals from −10 to −40 V. It was observed that the drain current was saturated as the drain voltage increased. Mobility determined from gate voltage dependence in the current saturated region was 0.014 $cm^2/V \cdot s$.

EXAMPLE 6

Synthesis of 6,13-dibromo-2,3,9,10-tetrapropylpentacene

<Synthesis of Intermediate>

6,13-dihydro-6,13-dihydroxy-2,3,9,10-tetrapropylpentacene was prepared in the same manner as in EXAMPLE 2.

<Method for Producing Polyacene Compound>

N-bromosuccinimide (462 mg) was dissolved in 20 mL of THF in a nitrogen atmosphere, and the resulting solution was cooled to −20° C., added to 0.28 mL of dimethyl sulfide dropwise, and stirred for 10 minutes. Then, the solution was added to a solution of 150 mg of 6,13-dihydro-6,13-dihydroxy-2,3,9,10-tetrapropylpentacene dissolved in 15 mL of THF dropwise, and then the reaction was carried out for 18 hours while being warmed up to room temperature.

The reaction product was distilled under a vacuum to remove the organic solvent, and the resulting residue was added to n-hexane and filtered. The residue was washed with acetonitrile and then with a 1/1 mixed solvent of n-hexane and benzene. This produced 37 mg of pure 6,13-dibromo-2,3,9,10-tetrapropylpentacene in a yield of 20%.

The resulting 6,13-dibromo-2,3,9,10-tetrapropylpentacene was analyzed by mass spectrometry. The results are given below.

FAB-HRMS (NBA): m/z=606, 604, 602

Moreover, it was analyzed by nuclear magnetic resonance spectroscopy (NMR) at room temperature with deuterated chloroform as a solvent. The results are given below.

$^1$H-NMR (ppm): δ1.07 (t, 12H), 1.75-1.78 (m, 8H), 2.76 (t, 8H), 7.77 (s, 4H), 9.06 (s, 4H)

<Method for Producing Organic Semiconductor Thin Film>

The 6,13-dibromo-2,3,9,10-tetrapropylpentacene synthesized above was dissolved in toluene in a nitrogen atmosphere, to produce a bluish purple solution (concentration: 0.2% by mass). The solution was spread on a silicon substrate in a nitrogen atmosphere to form a 100 nm thick thin film of 6,13-dibromo-2,3,9,10-tetrapropylpentacene.

The thin film of 6,13-dibromo-2,3,9,10-tetrapropylpentacene, prepared above, was analyzed by wide-angle X-ray diffraction analysis. The diffraction lines relevant to the (00n) plane (n=1, 2, 3 and 4) were observed, and the crystal lattice constant of the thin film was found to be 2.4 nm from the interplanar distance. Given that the 6,13-dibromo-2,3,9,10-tetrapropylpentacene molecule is 2.2 to 2.4 nm long in the major axis direction, it was found that the molecules formed the crystal in the thin film with the major axes of molecule being oriented toward a right angle to the substrate surface.

<Organic Semiconductor Device>

A silicon substrate (coated with a 200 nm thick thermally oxidized layer), heavily doped with an n-type dopant, was formed with a pattern of gold working as a source and drain electrodes. The gold electrode pattern comprises strips running in parallel to each other, spaced from each other by 50 μm (channel length). The pattern is 500 μm long (channel width).

The silicon substrate with the patterned electrodes was coated with a thin film of 6,13-dibromo-2,3,9,10-tetrapropylpentacene, in a manner similar to the above, to form a transistor structure.

The transistor was analyzed for current/voltage curve between the source and drain electrodes with the silicon substrate as the gate, where the gate voltage was changed at 10 V intervals from −10 to −40 V. It was observed that the drain current was saturated as the drain voltage increased. Mobility determined from gate voltage dependence in the current saturated region was 0.05 $cm^2/V \cdot s$.

EXAMPLE 7

Synthesis of 6,13-dibromo-2,3-dipropylpentacene

<Synthesis of Intermediate>

6,13-dihydro-6,13-dihydroxy-2,3-dipropylpentacene was prepared in the same manner as in EXAMPLE 3.

<Method for Producing Polyacene Compound>

N-bromosuccinimide (552 mg) was dissolved in 20 mL of THF in a nitrogen atmosphere, and the resulting solution was cooled to −20° C., added to 0.33 mL of dimethyl sulfide dropwise, and stirred for 10 minutes. Then, the resulting solution was added to a solution of 150 mg of 6,13-dihydro-6,13-dihydroxy-2,3-dipropylpentacene dissolved in 15 mL of THF dropwise, and then the reaction was carried out for 18 hours while being warmed up to room temperature.

The reaction product was distilled under a vacuum to remove the organic solvent, and the resulting residue was added to n-hexane and filtered. The residue was washed with a 5/1 mixed solvent of n-hexane and benzene and then with acetonitrile. This produced 30 mg of pure 6,13-dibromo-2,3-dipropylpentacene in a yield of 15%.

The resulting 6,13-dibromo-2,3-dipropylpentacene was analyzed by mass spectrometry. The results are given below.

FAB-HRMS (NBA): m/z=522, 520, 518

Moreover, it was analyzed by nuclear magnetic resonance spectroscopy (NMR) at room temperature with deuterated chloroform as a solvent. The results are given below.

$^1$H-NMR (ppm): δ1.09 (t, 6H), 1.76-1.82 (m, 4H), 2.77 (t, 4H), 7.40 (dd, 2H), 7.79 (s, 2H), 8.02 (dd, 2H), 9.10 (s, 2H), 9.20 (s, 2H)

<Method for Producing Organic Semiconductor Thin Film>

The 6,13-dibromo-2,3-dipropylpentacene synthesized above was dissolved in chloroform in a nitrogen atmosphere, to produce a bluish purple solution (concentration: 0.2% by mass). The solution was spread on a silicon substrate in a nitrogen atmosphere to form a 120 nm thick thin film of 6,13-dibromo-2,3-dipropylpentacene.

The thin film of 6,13-dibromo-2,3-dipropylpentacene, prepared above, was analyzed by wide-angle X-ray diffraction analysis. The diffraction lines relevant to the (00n) plane (n=1, 2, 3 and 4) were observed, and the crystal lattice constant of the thin film was found to be 2.4 nm from the interplanar distance. Given that the 6,13-dibromo-2,3-dipropylpentacene molecule is 2.0 to 2.4 nm long in the major axis direction, it was found that the molecules formed the crystal in the thin film with the major axes of molecule being oriented toward a right angle to the substrate surface.

<Organic Semiconductor Device>

A silicon substrate (coated with a 200 nm thick thermally oxidized layer), heavily doped with an n-type dopant, was formed with a pattern of gold working as a source and drain electrodes. The gold electrode pattern comprises strips running in parallel to each other, spaced from each other by 50 μm (channel length). The pattern is 500 μm long (channel width).

The silicon substrate with the patterned electrodes was coated with a thin film of 6,13-dibromo-2,3-dipropylpentacene in a manner similar to the above, to form a transistor structure.

The transistor was analyzed for current/voltage curve between the source and drain electrodes with the silicon substrate as the gate, where the gate voltage was changed at 10 V intervals from −10 to −40 V. It was observed that the drain current was saturated as the drain voltage increased. Mobility determined from gate voltage dependence in the current saturated region was 0.13 $cm^2/V·s$.

EXAMPLE 8

Synthesis of 6,13-dichloro-2,3-diethylpentacene

<Synthesis of Intermediate>

A solution of 150 mg of 2,3-diethyl-6,13-pentacenequinone dissolved in 30 mL of THF was added to 3.2 mL of a 1 mol/1000 mL THF solution of lithium triethylborohydride, and they were allowed to react with each other at room temperature for 2 hours in a nitrogen atmosphere. The resulting solution was neutralized with diluted aqueous hydrochloric acid, and the organic phase was separated, concentrated and dried under a vacuum to produce 2,3-diethyl-6,13-dihydro-6,13-dihydroxypentacene almost stoichiometrically.

<Method for Producing Polyacene Compound>

N-chlorosuccinimide (300 mg) was dissolved in 40 mL of dichloromethane in a nitrogen atmosphere, and the resulting solution was cooled to −20° C., added to 0.3 mL of dimethyl sulfide dropwise, and stirred for 10 minutes. Then, the resulting solution was added to a solution of 75 mg of 2,3-diethyl-6,13-dihydro-6,13-dihydroxypentacene dissolved in 4 mL of THF dropwise, and then the reaction was carried out for 18 hours while being warmed up to room temperature.

The reaction product was distilled under a vacuum to remove the organic solvent, and the resulting residue was washed acetonitrile thoroughly. This produced 25 mg of pure 6,13-dichloro-2,3-diethylpentacene in a yield of 30%.

The resulting 6,13-dichloro-2,3-diethylpentacene was analyzed by mass spectrometry. The results are given below.

FAB-HRMS (NBA): m/z=404, 402

Moreover, it was analyzed by nuclear magnetic resonance spectroscopy (NMR) at room temperature with deuterated chloroform as a solvent. The results are given below.

$^1$H-NMR (ppm): δ1.40 (t, 6H), 2.82 (q, 4H), 7.39 (dd, 2H), 7.78 (s, 2H), 8.00 (dd, 2H), 9.05 (s, 2H), 9.13 (s, 2H)

<Method for Producing Organic Semiconductor Thin Film>

The 6,13-dichloro-2,3-diethylpentacene synthesized above was dissolved in toluene in a nitrogen atmosphere, to produce a bluish purple solution (concentration: 0.2% by mass). The solution was spread on a silicon substrate in a nitrogen atmosphere to form a 90 nm thick thin film of 6,13-dichloro-2,3-diethylpentacene.

The thin film of 6,13-dichloro-2,3-diethylpentacene, prepared above, was analyzed by wide-angle X-ray diffraction analysis. The diffraction lines relevant to the (00n) plane (n=1, 2) were observed, and the crystal lattice constant of the thin film was found to be 1.7 nm from the interplanar distance. Given that the 6,13-dichloro-2,3-diethylpentacene molecule is 1.7 to 2.0 nm long in the major axis direction, it was found that the molecules formed the crystal in the thin film with the major axes of molecule being oriented toward a right angle to the substrate surface.

<Organic Semiconductor Device>

A silicon substrate (coated with a 200 nm thick thermally oxidized layer), heavily doped with an n-type dopant, was formed with a pattern of gold working as a source and drain electrodes. The gold electrode pattern comprises strips running in parallel to each other, spaced from each other by 50 μm (channel length). The pattern is 500 μm long (channel width).

The silicon substrate with the patterned electrodes was coated with a thin film of 6,13-dichloro-2,3-diethylpentacene in a manner similar to the above, to form a transistor structure.

The transistor was analyzed for current/voltage curve between the source and drain electrodes with the silicon substrate as the gate, where the gate voltage was changed at 10 V intervals from −10 to −40 V. It was observed that the drain current was saturated as the drain voltage increased. Mobility determined from gate voltage dependence in the current saturated region was $5\times10^{-4}$ $cm^2/V·s$.

EXAMPLE 9

Synthesis of 6,13-dichloro-2,3-(methylenedioxy)pentacene

<Synthesis of Intermediate>

A solution of 57 mg of 2,3-methylenedioxy-6,13-pentacenequinone dissolved in 25 mL of THF was added to 1.6 mL of a 1 mol/1000 mL THF solution of lithium triethylborohydride, and they were allowed to react with each other at room temperature for 1 hour in a nitrogen atmosphere. The resulting solution was neutralized with diluted aqueous hydrochloric acid, and the organic phase was separated, concentrated and dried under a vacuum to produce 6,13-dihydro-6,13-dihydroxy-2,3-(methylendioxy)pentacene almost stoichiometrically.

<Method for Producing Polyacene Compound>

N-chlorosuccinimide (250 mg) was dissolved in 40 mL of dichloromethane in a nitrogen atmosphere, and the resulting solution was cooled to −20° C., added to 0.3 mL of dimethyl sulfide dropwise, and stirred for 10 minutes. Then, the solution was added to a solution of 57 mg of 6,13-dihydro-6,13-dihydroxy-2,3-(methylenedioxy)pentacene dissolved in 3 mL of THF dropwise, and then the reaction was carried out for 18 hours while being warmed up to room temperature.

The reaction system was added to water to terminate the reaction. The reaction product was extracted with chloroform, and the organic phase separated was washed with a saturated NaCl aqueous solution and dried with magnesium sulfate. The organic phase was distilled under a vacuum to remove the organic solvent, and the resulting residue was reprecipitated in acetonitrile. This produced 8 mg of pure 6,13-dichloro-2,3-(methylenedioxy)pentacene in a yield of 13%.

The resulting 6,13-dichloro-2,3-(methylenedioxy)pentacene was analyzed by mass spectrometry. The results are given below.

FAB-HRMS (NBA): m/z=392, 390

Moreover, it was analyzed by nuclear magnetic resonance spectroscopy (NMR) at room temperature with deuterated chloroform as a solvent. The results are given below.

$^1$H-NMR (ppm): δ6.09 (s, 2H), 7.21 (s, 2H), 7.43 (dd, 2H), 8.04 (dd, 2H), 8.90 (s, 2H), 9.16 (s, 2H)

<Organic Semiconductor Device>

A silicon substrate (coated with a 200 nm thick thermally oxidized layer), heavily doped with an n-type dopant, was formed with a pattern of gold working as a source and drain electrodes. The gold electrode pattern comprises strips running in parallel to each other, spaced from each other by 50 μm (channel length). The pattern is 500 μm long (channel width).

The 6,13-dichloro-2,3-(methylenedioxy)pentacene synthesized above was dissolved in toluene in a nitrogen atmosphere, to produce a bluish purple solution (concentration: 0.2% by mass). The solution was spread on the silicon substrate with the patterned gold electrodes in a nitrogen atmosphere to form a thin film of 6,13-dichloro-2,3-(methylenedioxy)pentacene, to form a transistor structure.

The transistor was analyzed for current/voltage curve between the source and drain electrodes with the silicon substrate as the gate, where the gate voltage was changed at 10 V intervals from −10 to −40 V. It was observed that the drain current was saturated as the drain voltage increased. Mobility determined from gate voltage dependence in the current saturated region was $5 \times 10^{-3}$ cm$^2$/V·s.

INDUSTRIAL APPLICABILITY

The present invention is suitable in electronics, photonics, bioelectronics and so forth.

The invention claimed is:

1. A polyacene compound having a structure represented by the chemical formula (I):

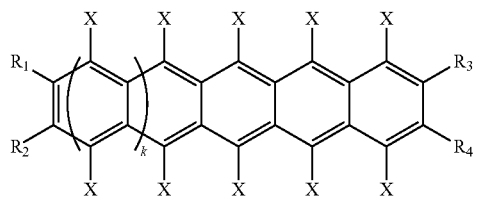

(I)

wherein at least one of $R_1$, $R_2$, $R_3$ and $R_4$ in the chemical formula (I) is/are an alkyl group having 1 to 15 atoms or an alkoxy group having 1 to 15 carbon atoms, and the other(s) is/are a hydrogen atom,
wherein two of Xs are each a halogen group and bound to the same acene ring and the others are each a hydrogen atom, and
wherein k is an integer of 1 to 5.

2. The polyacene compound according to claim 1, wherein $R_3$ and $R_4$ are each a hydrogen atom.

3. The polyacene compound according to claim 1, wherein the alkyl group or the alkoxy group has 2 to 15 carbon atoms.

4. The polyacene compound according to claim 1, wherein the alkyl group or the alkoxy group has 2 to 6 carbon atoms.

5. The polyacene compound according to claim 1, wherein k is 1 or 2.

6. An organic semiconductor thin film made of a polyacene compound having a structure represented by the chemical formula (I) and having crystallinity

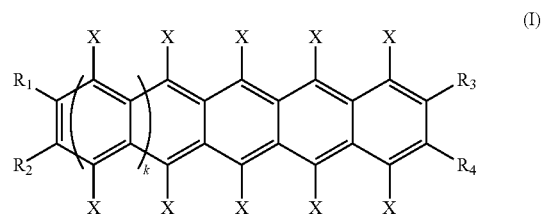

(I)

wherein at least one of $R_1$, $R_2$, $R_3$ and $R_4$ in the chemical formula (I) is/are an alkyl group having 1 to 15 carbon atoms or an alkoxy group having 1 to 15 carbon atoms, and the other(s) is/are a hydrogen atom;
wherein two of Xs are each a halogen group and bound to the same acene ring and the others are each a hydrogen atom; and
wherein k is an integer of 1 to 5.

7. The organic semiconductor thin film according to claim 6, wherein $R_3$ and $R_4$ are each a hydrogen atom.

8. The organic semiconductor thin film according to claim 6, wherein $R_1$, $R_2$, $R_3$ and $R_4$ have 2 to 15 carbon atoms, when they are functional groups.

9. The organic semiconductor thin film according to claim 6, wherein $R_1$, $R_2$, $R_3$ and $R_4$ have 2 to 6 carbon atoms, when they are functional groups.

10. The organic semiconductor thin film according to claim 6, wherein k is 1 or 2.

11. The crystalline organic semiconductor thin film according to claim 6 formed on a substrate, wherein the major axis of the molecule of the polyacene compound is oriented toward a right angle to the substrate surface.

12. An organic semiconductor device composed of the organic semiconductor thin film according to claim 6, at least partly.

13. A transistor comprising a gate electrode, dielectric layer, source electrode, drain electrode and semiconductor layer, wherein the semiconductor layer is composed of the organic semiconductor thin film according to claim 6.

14. A display device provided with pixel planes each composed of a number of pixels, wherein each of the pixels is provided with the organic semiconductor device according to claim 12 or transistor according to claim 13.

15. The display device according to claim 14, wherein an electrode, dielectric layer and semiconductor layer are formed in the organic semiconductor device or transistor by printing or coating a liquid.

* * * * *